United States Patent

Turnbull et al.

[11] Patent Number: 5,914,423
[45] Date of Patent: Jun. 22, 1999

[54] DIFLUOROBUTENES AND DIFLUOROBUTANES

[75] Inventors: Michael Drysdale Turnbull, Reading; Nigel James Willetts, Camberley; Steven Fitzjohn, Bracknell; Prafula Govind Kholia, Hayes; Harjindersingh Bansal, Forest Park; Alfred Glyn Williams, Emmets Park, all of United Kingdom

[73] Assignee: Zeneca, Limited, London, United Kingdom

[21] Appl. No.: 08/976,559

[22] Filed: Nov. 24, 1997

Related U.S. Application Data

[62] Division of application No. 08/286,142, Aug. 4, 1994, Pat. No. 5,728,833.

[30] Foreign Application Priority Data

| Aug. 5, 1993 | [GB] | United Kingdom | 9316219 |
| Aug. 5, 1993 | [GB] | United Kingdom | 9316220 |
| Dec. 13, 1993 | [GB] | United Kingdom | 9325453 |
| Dec. 13, 1993 | [GB] | United Kingdom | 9325455 |

[51] Int. Cl.⁶ ............. C07C 305/08; C07C 21/14; C07C 21/18
[52] U.S. Cl. ............. 558/54; 570/135; 570/136; 570/158
[58] Field of Search ............. 558/54; 570/135, 570/136, 158

[56] References Cited

U.S. PATENT DOCUMENTS

| 2,635,121 | 4/1953 | Smith et al. | 570/158 |
| 2,774,798 | 12/1956 | Davis et al. | 570/158 |
| 2,966,482 | 12/1960 | Bolstad et al. | 570/158 |
| 3,223,707 | 12/1965 | Brokke | 544/315 |
| 4,952,580 | 8/1990 | Martinez et al. | 514/236.2 |

FOREIGN PATENT DOCUMENTS

| 778748 | 7/1957 | United Kingdom | 570/158 |
| 982498 | 2/1965 | United Kingdom | 570/158 |
| 2270688 | 3/1994 | United Kingdom . | |
| 2270689 | 3/1994 | United Kingdom . | |
| 92/15555 | 9/1912 | WIPO . | |

OTHER PUBLICATIONS

Landbury et al., CA 79:65842, 1973.
Chem. Ber. 119, 2233–2248, 1986.
Chemical Abstracts, vol. 119, No. 9, Aug. 30, 1993, p. 1035, Abstracts No. 94942j, "Preparation of fluoroalkenyl group-–containing compounds as pesticides", Ruminski, P.G.

*Primary Examiner*—Yogendra N. Gupta
*Attorney, Agent, or Firm*—Dianne Burkhard

[57] ABSTRACT

A process for the preparation of a compound of formula (I):

$$HetSCH_2CH_2CH=CF_2 \qquad (I)$$

wherein Het is an optionally substituted 5- or 6-membered heterocyclic ring, which comprises reacting a compound of formula (II):

$$HetSH \qquad (II)$$

with a compound of formula (III):

$$CF_2=CHCH_2CH_2L \qquad (III)$$

wherein L is chlorine or bromine or a group $-OSO2R^a$ wherein $R^a$ is a C1–4 alkyl group or a phenyl group optionally substituted by a C1–4 alkyl group.

3 Claims, No Drawings

DIFLUOROBUTENES AND DIFLUOROBUTANES

This application is a division of application Ser. No. 08/286,142, filed Aug. 4, 1994 now U.S. Pat. No. 5,728,833.

This invention relates to a chemical process for the preparation of compounds useful as nematicides, and to intermediates of use in the process.

According to the present invention there is provided a process for the preparation of a compound of formula (I):

$$HetSCH_2CH_2CH=CF_2 \qquad (I)$$

wherein Het is an optionally substituted 5- or 6-membered heterocyclic ring, which comprises reacting a compound of formula (II):

$$HetSH \qquad (II)$$

with a compound of formula (III):

$$CF_2=CHCH_2CH_2L \qquad (III)$$

wherein L is chlorine or bromine or a group —$OSO_2R^a$ wherein $R^a$ is a C1–4 alkyl group or a phenyl group optionally substituted by a C1–4 alkyl group.

The 5- or 6-membered heterocyclic ring may be for example an oxazole, isoxazole, thiazole, isothiazole, imidazole, 1,2,4- or 1,3,4-oxadiazole, 1,2,4- or 1,3,4-thiadiazole, pyridine, pyridazine, pyrimidine, or pyrazine ring, or, except in the case of oxadiazoles or thiadiazoles, a benz derivative of any of these heterocyclic rings. The optional substituents may comprise one or more aliphatic or alicyclic radicals of 1 to 8 or more carbon atoms, for example alkyl, alkenyl, or alkynyl radicals of 1 to 6 carbon atoms, cycloalkyl and cycloalkyl radicals; halogen; haloalkyl; haloalkenyl; alkoxy; alkenoxy; alkoxyalkyl; haloalkoxy; haloalkenoxy; alkylthio; haloalkylthio; cyano; nitro; amino; amino substituted with one or two alkyl groups each having one to three carbon atoms; hydroxy; acylamino; carboxy or aliphatic ester thereof having one to six or more carbon atoms; or carbamoyl optionally substituted with one or two alkyl groups each having from one to six carbon atoms, or by a polymethylene di-radical forming, with the nitrogen atom of the carbamoyl group, a 5- or 6-membered ring.

According to one aspect, the present invention provides a process for the preparation of a compound of formula (IV) wherein X is O or S, $R^1$, $R^2$, $R^3$, and $R^4$ are independently hydrogen, alkyl, alkenyl, alkynyl, cycloalkyl, alkylcycloalkyl, halogen, haloalkyl, haloalkenyl, alkoxy, alkenoxy, alkoxyalkyl, haloalkoxy, haloalkenoxy, alkylthio, haloalkylthio, cyano, nitro, amino, $NR^5R^6$, hydroxy, amino, acylamino, —$CO_2R^7$, $CONR^6R^7$; or $R^1$ and $R^2$ when taken together form a 5- or 6-membered ring; $R^6$ and $R^7$ are hydrogen or $C_{1-4}$ alkyl; $R^5$ is $C_{1-4}$ alkyl, which comprises reaction of a compound of formula (V) with a compound of formula (VI) wherein $R^a$ is a $C_{1-4}$ alkyl group or a phenyl group optionally substituted with a $C_{1-4}$ alkyl group.

When any of $R^1$ to $R^4$ is an alkyl group it can be straight or branched chain and is preferably $C_{1-4}$ alkyl, in particular, methyl, ethyl, propyl, isopropyl, n-butyl, iso-butyl, sec-butyl or tertiary butyl.

When any of $R^1$ to $R^4$ is an alkenyl or alkynyl group it can be straight or branched chain and preferably contains up to 6 carbon atoms, for example, allyl or propargyl.

When any of $R^1$ to $R^4$ is a cycloalkyl or alkylcycloalkyl group, it preferably contains from 3 to 7 carbon atoms, for example, cyclopropyl, cyclopentyl, cyclohexyl or methylcyclopropyl.

When any of $R^1$ to $R^4$ is halogen, it is preferably fluorine, chlorine or bromine.

When any of $R^1$ to $R^4$ is a haloalkyl or haloalkenyl group, the halogen is preferably chlorine, fluorine or bromine, the alkyl moiety is preferably $C_{1-4}$ alkyl, for example, trifluoromethyl, trifluoroethyl or pentafluoroethyl and the alkenyl is preferably $C_{2-6}$ alkenyl.

When any of $R^1$ to $R^4$ is an alkoxy, alkenoxy or alkoxyalkyl group it can be straight or branched chain and preferably contains up to 6 carbon atoms, for example, a methoxy, ethoxy, propoxy, butoxy, butenoxy, methoxymethyl, methoxyethyl or ethoxymethyl group.

When any of $R^1$ to $R^4$ is a haloalkoxy group, it can be straight or branched chain and preferably contains up to 6 carbon atoms. The halogen is preferably chlorine, fluorine or bromine. Particular examples are trifluoromethoxy, trifluoroethoxy or pentafluoroethoxy.

When any of $R^1$ to $R^4$ is a haloalkenoxy group, it can be straight or branched chain and preferably contains up to 6 carbon atoms. The halogen is preferably chlorine, fluorine or bromine. Particular examples are $OCH_2CH_2CH=CF_2$ and $OCH_2CH_2CH=CHF$.

When any of $R^1$ to $R^4$ is an alkylthio group, the alkyl preferably contains up to 4 carbon atoms. For example, —S-methyl, —S-ethyl, —S-propyl, S-butyl.

When any of $R^1$ to $R^4$ is an haloalkylthio group, the alkyl preferably contains up to 4 carbon atoms, and the halogen group is preferably, fluorine, chlorine or bromine, for example, —S—$CF_3$, —S—$C_2H_4F$, —$S(CH_2)_2CH_2F$, $SCBrF_2$, $SCClF_2$ and —S—$CH_2CF_3$.

When any of $R^1$ to $R^4$ is $NR^5R^6$, it is preferably $NHCH_3$, $N(CH_3)_2$ or $N(C_2H_5)_2$.

When any of $R^1$ to $R^4$ is acylamino, it is preferably $NHCOCH_3$ or $NHCOC_2H_5$.

When any of $R^1$ to $R^4$ is $CO_2R^7$, $R^7$ is preferably hydrogen, methyl or ethyl.

When any of $R^1$ to $R^4$ is $CONR^5R^7$, $R^5$ and $R^7$ are preferably hydrogen, methyl or ethyl. Especially preferred is $CONH_2$.

When $R^1$ and $R^2$ are taken together to form a 5- or 6-membered ring, it is preferably a carbocylic ring, for example, —$(CH_2)_3$—, —$(CH_2)_4$— or —CH=CH—CH=CH—.

Of particular interest are compounds of formula (I) where X is O or S, and $R^1$ to $R^4$ are independently hydrogen, fluorine, chlorine, methyl, ethyl, methoxy, ethoxy, trifluoromethyl, trifluoromethoxy, trifluoroethoxy, $SCH_3$ and $SCH_2CF_3$.

The nematicidal properties of compounds of formula (IV) and oxidised derivatives thereof are described in published UK Patent Application No. 2,270,689A.

Examples of the compounds of formula (IV) which may be prepared according to the process of the invention are set out in Table I.

TABLE I

| COMPOUND NO. | $R^1$ | $R^2$ | $R^3$ | $R^4$ | X |
|---|---|---|---|---|---|
| 1 | H | H | H | H | S |
| 2 | H | H | H | H | O |
| 3 | H | F | H | H | O |
| 5 | $NO_2$ | H | H | H | O |
| 6 | $NH_2$ | H | H | H | O |
| 7 | $CH_3$ | H | H | H | S |
| 8 | H | F | F | H | O |

TABLE I-continued

| COMPOUND NO. | $R^1$ | $R^2$ | $R^3$ | $R^4$ | X |
|---|---|---|---|---|---|
| 10 | $CO_2CH_3$ | H | H | H | O |
| 11 | $NHCOCH_3$ | H | H | H | S |
| 12 | H | H | H | H | S |
| 13 | COOH | H | H | H | S |
| 15 | F | H | H | H | S |
| 16 | H | H | H | $CH_3$ | S |
| 17 | H | H | $CH_3$ | H | O |
| 18 | H | H | $CH_2CH=CH_2$ | H | O |
| 19 | H | H | $^cC_3H_5$ | H | O |
| 20 | H | H | Cl | H | O |
| 21 | H | H | CN | H | S |
| 22 | H | $CH_3$ | H | H | S |
| 23 | H | $CH_2CH=CH_2$ | H | H | O |
| 24 | H | $^cC_3H_5$ | H | H | O |
| 26 | H | $C_6H_5$ | H | H | O |
| 27 | $CH_3$ | $CH_3$ | H | H | O |
| 28 | Cl | Cl | H | H | S |
| 29 | F | Cl | H | H | O |
| 30 | $OCH_3$ | H | $NHCOCH_3$ | H | O |
| 31 | $OCH_3$ | H | $OCH_3$ | H | O |
| 32 | $OCH_3$ | $OCH_3$ | H | H | O |
| 33 | $1\text{-}CH_3\text{---}^cC_3H_5$ | H | H | H | S |
| 34 | OH | F | H | H | O |
| 35 | OH | H | Cl | H | S |
| 36 | H | H | $CO_2CH_3$ | H | O |
| 37 | $OCH_2CF_3$ | H | H | H | S |
| 40 | H | H | $CH_2OCH_3$ | H | S |
| 41 | H | $CH_3$ | H | H | O |
| 42 | H | H | CN | H | O |
| 43 | —CH=CH—CH=CH— | | H | H | S |
| 44 | —CH=CH—CH=CH— | | H | H | O |

$^c$ indicates a cyclic substituent

According to the process of the invention, a compound of Formula (V) wherein $R^1$, $R^2$, $R^3$, $R^4$, and X have any of the meanings given above, is reacted with a compound of Formula (VI) wherein $R^a$ is a $C_{1-4}$ alkyl group, especially methyl, or a phenyl group optionally substituted with a $C_{1-4}$ alkyl group, especially para-tolyl, under conditions well known in the art for such displacement reactions, for example in the presence of a mild base such as an alkali metal carbonate, for example potassium or sodium carbonate, in an inert solvent, at a temperature in the range from 40° C. to 100° C., and most conveniently at the reflux temperature of a suitable inert solvent such as acetone which has a boiling point within this range.

Compounds of Formula (VI) may be prepared by the following sequence of reactions. Hydrogen bromide is reacted with the commercially available compound of Formula (VII) under standard conditions for an addition reaction, for example by passing hydrogen bromide gas through a solution of the compound of Formula (VII) in an inert solvent to give the compound of Formula (VIII). The compound of Formula (VIII) is then reacted with the silver salt of a sulphonic acid of Formula $R^aSO_3H$, wherein $R^a$ has the meaning given above, for example the silver salt of 4-methylbenzenesulphonic acid (silver tosylate) or the silver salt of methanesulphonic acid (silver mesylate), preferably in an inert solvent in the absence of light, to give the corresponding compound of Formula (IX). Debromofluorination of the compound of Formula (IX), for example by reaction with zinc, preferably in the presence of a suitable catalyst such as iodine, gives the compound (VI), wherein $R^a$ has the meanings given above.

It will be appreciated by those skilled in the art that compounds of Formula (V) exist in tautomeric equilibrium between the equivalent 2-mercapto and 2-thione forms. For the sake of convenience, the compounds are referred to herein in their 2-mercapto form unless otherwise stated.

Compounds of Formula (V) are commercially available or may be prepared from commercially available precursors by standard procedures well known in the art. Typical procedures suitable for the preparation of many of the relevant compounds of Formula (V) and their precursors may be found in the following standard references: Comprehensive Heterocyclic Chemistry (Published by Pergamon, Edited by Katritzky and Rees), 1984, e.g. pages 177–331; Journal of Organic Chemistry, 19, 758–766 (1954); Heterocyclic Compounds (Published by Wiley, Edited by Elderfield), Volume 5; Organic Compounds of Sulphur, Selenium and Tellurium (Published by The Chemical Society, Specialist Reports), Volumes 3, 4 and 5; Warburton et al, Chemical Reviews, 57, 1011–1020 (1957). By way of example, many of the compounds of formula (V) where X is oxygen may be prepared by reacting a correspondingly substituted 2-aminophenol or a salt thereof, with thiophosgene, in an inert solvent such as diethyl ether or chloroform, and optionally in the presence of a base, such as potassium carbonate, and/or water. Also by way of example, many of the compounds of formula (V) where X is sulphur may be prepared by the Herz Reaction (Warburton et al, Chemical Reviews, 57, 1011–1020 (1957)) in which appropriately substituted anilines are reacted sequentially with disulphur dichloride and aqueous sodium hydroxide to produce the corresponding 2-mercapto aniline derivative, which is then reacted with carbon disulphide to produce the 2-mercaptobenzthiazole of formula (V). Benzthiazoles of formula (V) may also be prepared from appropriately substituted N-phenylthioureas by oxidation (for example in the presence of molecular bromine) and replacement of the amino group of the resulting 2-aminobenzthiazole with a 2-mercapto group by reaction with a base and carbon disulphide or by diazotisation, reaction with a halide and displacement of the 2-halo group using NaSH or thiourea. N-phenylthioureas are available by reaction of the corresponding anilines with ammonium thiocyanate. Compounds of Formula (V) may also be prepared by reaction of the correspondingly substituted 2-halonitrobenzene by reaction with sodium sulphide, sulphur ($S_8$), and carbon disulphide, or by reaction of the correspondingly substituted phenyl isothiocyanate with sulphur ($S_8$) to produce the corresponding mercaptobenzthiazole. All of these reactions are well documented in the chemical literature. The choice of the appropriate procedure will depend upon the particular nuclear substitution pattern required and is within the normal skill of the art.

A general procedure for the preparation of 2-mercaptobenzthiazoles (from the corresponding 2-aminobenzthiazoles) is illustrated by the following preparation of 6-fluoro-2-mercaptobenzthiazole (Ref. J.Het. Chem. (1980) 17 1325).

A solution of 2-amino-6-fluorobenzthiazole (10.0 g) in water (100 cm$^3$) containing sodium hydroxide (50.0 g) was stirred and heated to reflux for 18 hours, cooled to the ambient temperature and filtered. Carbon disulphide (17.5 cm$^3$) was added to the filtrate and the mixture was heated to reflux for 4 hours, cooled to the ambient temperature, diluted with water and neutralised with acetic acid. The fawn solid which precipitated was filtered from solution, washed with water and dried by suction to give the title product, mp above 260° C., M$^+$=185.

The following compounds were prepared using the above method.

(i) 2-Mercapto-4-methylbenzthiazole: mp above 260° C.; M$^+$=181; yellow solid (ii) 2-Mercapto-6-methylbenzthiazole: mp 248° C.; $M^+$=181; yellow solid A general procedure for the preparation of 2-mercaptobenzoxazoles (from the corresponding 2-aminophenol) is illustrated by the following preparation of 2-mercapto-5-methylbenzoxazole.

To a brown solution of 2-amino-5-methylphenol (5 g) in 2 M NaOH (80 cm$^3$) stirring at the ambient temperature was added carbon disulphide and the reaction mixture was stirred for 5 days. The solution was acidified to pH 4 by the addition of concentrated hydrochloric acid, causing formation of a beige precipitate. The precipitate was filtered and dried by suction to give the title product as a free flowing beige powder (4.06 g). $^1$H NMR (DMSO): δ 13.9 (1H,br s); 7.5(1H,d); 7.18(1H,d); 7.15(1H,s); 2.49(3H,s) ppm.

According to a further aspect of the present invention there is provided a process for the preparation of a compound of formula (X) wherein $R^8$, $R^9$, $R^{10}$ and $R^{11}$ are independently hydrogen, alkyl, alkenyl, alkynyl, cycloalkyl, alkylcycloalkyl, halogen, haloalkyl, haloalkenyl, alkoxy, alkenoxy, alkoxyalkyl, haloalkoxy, haloalkenoxy, alkylthio, haloalkylthio, —SCH2CH2CH=CF2, cyano, nitro, amino, NR12R13, hydroxy, acylamino, —CO2R$^{14}$, —O(CH2) mCO2R14, CONR13R14, phenyl, phenoxy, benzyl or benzyloxy, the phenyl group or phenyl moiety of the benzyl group being optionally substituted in the ring; or $R^9$ and $R^{10}$ when taken together form a 5- or 6-membered ring; m is 1 or 2; $R^{13}$ and $R^{14}$ are hydrogen or $C_{1-4}$ alkyl; $R^{11}$ is $C_{1-4}$ alkyl; provided that at least one of R8 to R11 is SCH2CH2CH=CF2, which comprises reaction of a compound of formula (XI) with a compound of formula (VI) wherein $R^a$ is a $C_{1-4}$ alkyl group or a phenyl group optionally substituted with a C1–4 alkyl group.

When any of $R^8$ to $R^{11}$ is an alkyl group it can be straight or branched chain and is preferably $C_{1-4}$ alkyl, in particular ethyl, propyl, isopropyl, n-butyl, iso-butyl, sec-butyl or tertiary butyl.

When any of $R^8$ to $R^{11}$ is an alkenyl or alkynyl group it can be straight or branched chain and preferably contains up to 6 carbon atoms, for example, allyl or propargyl.

When any of $R^8$ to $R^{11}$ is a phenyl, phenoxy, benzyl or benzyloxy group, the phenyl moiety may be optionally substituted with halogen, (for example, chlorine, fluorine, or bromine), cyano, alkyl, haloalkyl, alkoxy or haloalkoxy, the alkyl group being preferably $C_{1-4}$ alkyl and the alkoxy group being preferably $C_{1-6}$ alkyl. Examples of such groups are 2-, 3- or 4-fluorophenyl, 2-, 3- or 4-chlorophenyl, 2,4- or 2,6-difluorophenyl, 2,4- or 2,6- dichlorophenyl, 2-chloro-4-fluorophenyl, 2-chloro-6-fluorophenyl, 2-fluoro-4-chlorophenyl, 2-fluoro-6-chlorophenyl, 2-,3- or 4-methoxyphenyl, 2, 4-dimethoxyphenyl, 2-, 3-, or 4-ethoxyphenyl, 2-, 3- or 4-methylphenyl, 2-, 3- or 4-ethylphenyl, 2-, 3- or 4-trifluoromethylphenyl, and the corresponding ring substituted benzyl, phenoxy and benzyloxy groups.

When any of $R^8$ to $R^{11}$ is a cycloalkyl or alkylcycloalkyl group, it preferably contains from 3 to 7 carbon atoms, for example, cyclopropyl, cyclopentyl, cyclohexyl or methylcyclopropyl.

When any of $R^8$ to $R^{11}$ is halogen, it is preferably fluorine, chlorine or bromine.

When any of $R^8$ to $R^{11}$ is haloalkyl, the halogen is preferably chlorine, fluorine or bromine, the alkyl moiety is preferably $C_{1-4}$ alkyl, for example, trifluoromethyl, trifluoroethyl or pentafluoroethyl, and the alkenyl moiety is preferably $C_{2-6}$ alkenyl.

When any of $R^8$ to $R^{11}$ is an alkoxy, alkenoxy or alkoxyalkyl group, it can be straight or branched chain and preferably contains up to 6 carbon atoms, for example, methoxy, ethoxy, propoxy, butoxy, butenoxy, methoxymethyl, methoxyethyl or ethoxymethyl.

When any of $R^8$ to $R^{11}$ is a haloalkoxy group, it can be straight or branched chain and preferably contains up to 6 carbon atoms. The halogen is preferably chlorine, fluorine or bromine. Particular examples are trifluoromethoxy, trifluoroethoxy and pentafluoroethoxy.

When any of $R^8$ to $R^{11}$ is a haloalkenoxy group, it can be straight or branched chain and preferably contains up to 6 carbon atoms. The halogen is preferably chlorine, fluorine or bromine. Particular examples are $OCH_2CH_2CH=CF_2$ and $OCH_2CH_2CH=CHF$.

When any of $R^8$ to $R^{11}$ is an alkylthio group, the alkyl preferably contains up to 4 carbon atoms. For example, —S-methyl, —S-ethyl, —S-propyl, S-butyl.

When any of $R^8$ to $R^{11}$ is a haloalkylthio group, the alkyl preferably contains up to 4 carbon atoms, i.e. methyl, ethyl, propyl and butyl. The halogen group is preferably, fluorine, chlorine or bromine, for example, —S—CF3, —SC2H4F, —S(CH2)2CH2F, SCBrF2, SCClF2 and S—CH2CF3.

When any of $R^8$ to $R^{11}$ is $-SCH_2CH_2CH=CF_2$ it is preferably a substituent in the $R^8$ or $R^{11}$ position, or alternatively, in both the $R^8$ and $R^{11}$ positions or in both the $R^8$ and $R^{10}$ positions.

When any of $R^8$ to $R^{11}$ is $NR^{12}R^{13}$, it is preferably $NHCH_3$, $N(CH_3)_2$ or $N(C_2H_5)_2$.

When any of $R^8$ to $R^{11}$ is acylamino, it is preferably $NHCOCH_3$ or $NHCOC_2H_5$.

When any of $R^8$ to $R^{11}$ is $CO_2R^{14}$, $R^{14}$ is preferably hydrogen, methyl or ethyl.

When any of $R^8$ to $R^{11}$ is $O(CH_2)_mCO_2R^{14}$, m is preferably 2 and $R^{14}$ is preferably hydrogen, methyl or ethyl.

When any of $R^8$ to $R^{11}$ is $CONR^{13}R^{14}$, $R^{13}$ and $R^{14}$ are preferably hydrogen, methyl or ethyl. Especially preferred is $CONH_2$.

When $R^9$ and $R^{10}$ are taken together to form a 5- or 6-membered ring, it is preferably a carbocylic ring, for example, $-(CH_2)_3-$, $-(CH_2)_4-$ or $-CH=CH-CH=CH-$.

Of particular interest are the compounds of formula (X) where $R^8$ is selected from $C_{1-4}$ alkyl, $C_{1-4}$ haloalkyl, halogen, $C_{1-6}$ alkoxy or hydroxy, $R^9$ is selected from hydrogen or $C_{1-4}$ alkyl, $R^{10}$ is selected from hydrogen, $C_{1-4}$ alkyl, $C_{1-6}$ alkoxy, hydroxy or halogen and $R^{11}$ is $SCH_2CH_2CH=CF_2$. Or alternatively, the compounds of formula (IX) where $R^8$ is phenyl, phenoxy, benzyl or benzyloxy, the phenyl group or phenyl moiety of the benzyl group being optionally substituted, $R^9$ is hydrogen or $C_{1-4}$ alkyl, $R^{10}$ is selected from hydrogen, $C_{1-4}$ alkyl, $C_{1-6}$ alkoxy, hydroxy or halogen and $R^{11}$ is $-SCH_2CH_2CH=CF_2$.

Also of particular interest are the compounds of formula (X) where $R^8$ is $SCH_2CH_2CH=CF_2$, $R^9$ is selected from hydrogen and $C_{1-4}$ alkyl, $R^{10}$ is selected from hydrogen, $C_{1-4}$ alkyl, $C_{1-4}$ haloalkyl, $C_{1-6}$ alkoxy, $C_{1\,6}$ haloalkoxy, $R^{11}$ is selected from hydrogen, $C_{1-4}$ alkyl and optionally substituted phenyl.

The nematicidal properties of compounds of formula (X) and oxidised derivatives thereof are described in published UK Patent Application No. 2,270,688A.

Examples of the compounds of formula (X) which may be prepared according to the process of the invention are set out in Table II.

TABLE II

| COMPOUND NO. | $R^8$ | $R^9$ | $R^{10}$ | $R^{11}$ |
|---|---|---|---|---|
| 2.1 | H | H | H | $SCH_2CH_2CH=CF_2$ |
| 2.3 | $CF_3$ | H | $OCH_3$ | $SCH_2CH_2CH=CF_2$ |
| 2.4 | $C_6H_5$ | H | H | $SCH_2CH_2CH=CF_2$ |
| 2.5 | $SCH_2CH_2CH=CF_2$ | H | H | H |
| 2.6 | $OC_2H_5$ | $CH_3$ | H | $SCH_2CH_2CH=CF_2$ |
| 2.7 | $OCH_3$ | H | $n-C_3H_7$ | $SCH_2CH_2CH=CF_2$ |
| 2.9 | $OC_3H_9$ | H | H | $SCH_2CH_2CH=CF_2$ |
| 2.10 | $OCH_2CH=CHCH_3$ | H | H | $SCH_2CH_2CH=CF_2$ |
| 2.11 | OH | H | $n-C_3H_7$ | $SCH_2CH_2CH=CF_2$ |
| 2.12 | $CF_3$ | H | H | $SCH_2CH_2CH=CF_2$ |
| 2.13 | $SCH_2CH_2CH=CF_2$ | H | $OCH_2CF_3$ | H |
| 2.14 | $CH_3$ | H | $OCH_2CH_3$ | $SCH_2CH_2CH=CF_2$ |
| 2.15 | Cl | H | $n-C_3H_7$ | $SCH_2CH_2CH=CF_2$ |
| 2.16 | $OCH_2C_6H_5$ | H | H | $SCH_2CH_2CH=CF_2$ |
| 2.17 | $OCH_2CO_2CH_3$ | H | H | $SCH_2CH_2CH=CF_2$ |
| 2.18 | $n-C_3H_7$ | H | H | $SCH_2CH_2CH=CF_2$ |
| 2.19 | $OCH_2(4-Cl-C_6H_4)$ | H | H | $SCH_2CH_2CH=CF_2$ |
| 2.20 | $OCH_2CO_2H$ | H | H | $SCH_2CH_2CH=CF_2$ |
| 2.21 | $OCH_2CF_3$ | H | $CH(CH_3)_2$ | $SCH_2CH_2CH=CF_2$ |
| 2.22 | Cl | H | $CH(CH_3)_2$ | $SCH_2CH_2CH=CF_2$ |
| 2.23 | $O(CH_2)_2CO_2CH_3$ | H | H | $SCH_2CH_2CH=CF_2$ |
| 2.24 | $OCH_3$ | H | $CH(CH_3)_2$ | $SCH_2CH_2CH=CF_2$ |
| 2.25 | $CH(CH_3)_2$ | H | H | $SCH_2CH_2CH=CF_2$ |
| 2.26 | $SCH_2CH_2CH=CF_2$ | H | $CH_3$ | $C_6H_5$ |
| 2.27 | $SCH_2CH_2CH=CF_2$ | H | H | $CH_3$ |
| 2.28 | $OCH_3$ | | $-(CH_2)_4-$ | $SCH_2CH_2CH=CF_2$ |
| 2.29 | $CH_3$ | H | H | $SCH_2CH_2CH=CF_2$ |
| 2.30 | $CH_3$ | H | H | $SCH_2CH_2CH=CF_2$ |
| 2.31 | H | $C(CH_3)_3$ | H | $SCH_2CH_2CH=CF_2$ |
| 2.32 | H | $CF_3$ | H | $SCH_2CH_2CH=CF_2$ |
| 2.33 | H | $CH(CH_3)_2$ | H | $SCH_2CH_2CH=CF_2$ |
| 2.34 | H | Cl | H | $SCH_2CH_2CH=CF_2$ |
| 2.35 | H | $C_6H_5$ | H | $SCH_2CH_2CH=CF_2$ |
| 2.36 | $SCH_2CH_2CH=CF_2$ | H | H | $SCH_2CH_2CH=CF_2$ |
| 2.37 | $OCH_2CH_2CH=CF_2$ | H | H | $SCH_2CH_2CH=CF_2$ |
| 2.38 | H | | $-(CH_2)_3-$ | $SCH_2CH_2CH=CF_2$ |
| 2.39 | $CH_3$ | $CH_3$ | $CH_3$ | $SCH_2CH_2CH=CF_2$ |
| 2.40 | $-SCH_2CH_2CH=CF_2$ | $CH_3$ | $SCH_2CH_2CH=CF_2$ | H |
| 2.41 | $-C\equiv CH$ | H | H | $SCH_2CH_2CH=CF_2$ |
| 2.42 | CN | H | H | $SCH_2CH_2CH=CF_2$ |
| 2.43 | $4-F-C_6H_4$ | H | H | $SCH_2CH_2CH=CF_2$ |
| 2.44 | $4-F-C_6H_4$ | H | H | $SCH_2CH_2CH=CF_2$ |
| 2.45 | $4-CF_3-C_6H_4CH_2$ | H | H | $SCH_2CH_2CH=CF_2$ |
| 2.46 | $^cC_3H_5$ | H | H | $SCH_2CH_2CH=CF_2$ |
| 2.47 | $1-CH_3-^cC_3H_5$ | H | H | $SCH_2CH_2CH=CF_2$ |
| 2.48 | $CH_2CF_3$ | H | H | $SCH_2CH_2CH=CF_2$ |
| 2.49 | $OCH_2CF_3$ | H | Cl | $SCH_2CH_2CH=CF_2$ |
| 2.50 | $CH_2OCH_3$ | H | H | $SCH_2CH_2CH=CF_2$ |
| 2.51 | Cl | H | Cl | $SCH_2CH_2CH=CF_2$ |
| 2.52 | $-SCH_2CH_2CH=CF_2$ | H | $OCH_2CH_2CH=CF_2$ | H |
| 2.53 | F | H | H | $SCH_2CH_2CH=CF_2$ |
| 2.54 | $SCH_3$ | H | F | $SCH_2CH_2CH=CF_2$ |
| 2.55 | $C(CH_3)_3$ | H | H | $SCH_2CH_2CH=CF_2$ |
| 2.56 | $C(CH_3)_3$ | H | H | $SCH_2CH_2CH=CF_2$ |
| 2.57 | H | | $-CH=CH-CH=CH-$ | $SCH_2CH_2CH=CF_2$ |
| 2.60 | OH | | $-CH=CH-CH=CH-$ | $SCH_2CH_2CH=CF_2$ |

$^c$indicates a cyclic substituent

According to the process of the invention, a compound of Formula (XI) wherein $R^8$, $R^9$, $R^{10}$ and $R^{11}$ have any of the meanings given above is reacted with a compound of Formula (VI) wherein $R^a$ is a $C_{1-4}$ alkyl group, especially methyl, or a phenyl group optionally substituted with a $C_{1-4}$ alkyl group, especially para-tolyl, under conditions well known in the art for such displacement reactions, for example in the presence of a mild base such as an alkali metal carbonate, for example potassium or sodium carbonate, in an inert solvent, at a temperature in the range from 40° C. to 100° C., and most conveniently at the reflux temperature of a suitable inert solvent such as acetone which has a boiling point within this range.

It will be appreciated by those skilled in the art that compounds of Formula (XI) exist in tautomeric equilibrium between the equivalent mercapto and thione forms. For the sake of convenience, the compounds are referred to herein in their mercapto form unless otherwise stated.

Compounds of Formula (XI) are commercially available or may be prepared from commercially available precursors by standard procedures well known in the art. Typical procedures for the preparation of the relevant compounds of Formula (XI) and their precursors may be found in the following standard references: The Pyrimidines, D J Brown (Published by Wiley, 1962); The Chemistry of Heterocyclic Compounds, Vol 16, Supplement I and Supplement II (Edited by A Weissberger). The choice of the most suitable process is dependent upon the particular substitution pattern required and will be readily determined by those skilled in the art from the standard methods.

A general two step procedure for the preparation of 4-aryl-, 4-alkyl-, or 4-alkoxyalkyl- 2-pyrimidinethiones from the corresponding methyl ketone is given by R F Abdulla and R S Brinkmeyer in Tetrahedron 35, 1675 (1979). The following intermediate compounds were prepared according to this procedure. The starting materials were commercially available.

(a) 4-phenyl-2(1H)-pyrimidinethione. $^1$H NMR (DMSO): δ 3.5(1H, br s); 7.58(1H,d); 7.60–7.78(3H,m); 8.24(1H,d); 8.30(2H,dd) (yellow solid).

(b) 4-(4-fluorophenyl)-2(1H)-pyrimidinethione. $^1$H NMR (DMSO): δ 7.44–7.54(2H,m); 7.56(1H,d); 8.20(1H,d) 8.30–8.40(2H,m); 13.90(1H, br s) (yellow solid).

(c) 4-cyclopropyl-2(1H)-pyrimidinethione. $^1$H NMR (DMSO): δ 1.12–1.28(4H,m); 2.12–2.24(1H,m); 6.90(1H, d); 7.98(1H,d) (orange solid).

(d) 4-(1-methylcyclopropyl)-2(1H)-pyrimidinethione. $^1$H NMR (DMSO): δ 1.00–1.08(2H,m); 1.30–1.38(2H,m); 1.48 (3H,s); 6.84(1H,d); 7.92(1H,d); 13.54(1H,br s) (yellow solid).

In a further aspect, the invention provides a process of preparing a compound of formula (IV) as hereinbefore defined, which comprises reaction of a compound of formula (V) as hereinbefore defined with 4-bromo-1,1-difluorobut-1-ene.

In a still further aspect, the invention provides a process of preparing a compound of formula (X) as hereinbefore defined, which comprises reaction of a compound of formula (XI) as hereinbefore defined with 4-bromo-1,1-difluorobut-1-ene.

According to the last two foregoing aspects of the invention, a compound of formula (V) as hereinbefore defined, or a compound of formula (XI) as hereinbefore defined, is reacted with 4-bromo-1,1-difluorobut-1-ene, under conditions well known in the art for such displacement reactions, for example in the presence of a mild base such as an alkali metal carbonate, for example potassium or sodium carbonate, in an inert solvent, at a temperature in the range from 40 to 100° C., and most conveniently at the reflux temperature of a suitable inert solvent such as acetone which has a boiling point within this range.

4-Bromo-1,1-difluorobut-1-ene may be prepared by the following sequence of reactions: hydrogen bromide is reacted with the commercially available compound 4-bromo-1,1,2-trifluorobut-1-ene having the formula (VII), under standard conditions for an addition reaction, for example by passing hydrogen bromide gas through a solution of 4-bromo-1,1,2-trifluorobut-1-ene in an inert solvent, optionally in the presence of a free radical generator (e.g. benzoyl peroxide), to give 1,4-dibromo-1,1,2-trifluorobutane (Formula VIII). This compound is then treated with a debromofluorinating agent, which removes a bromine atom and a fluorine atom from the 1,4-dibromo-1,1,2-trifluorobutane to give 4-bromo-1,1-difluorobut-1-ene. Examples of debromofluorinating agents include zinc, magnesium, and aluminium. 4-Bromo-1,1-difluorobut-1-ene is a relatively volatile compound, and if the debromofluorination reaction is done in an organic solvent (e.g. acetone), in order to minimise losses it may be preferable to react the solution of the product obtained from the bromodefluorination reaction directly with the mercaptopyrimidine, mercaptobenzoxazole, or mercaptobenzthiazole, rather than to isolate and purify the 4-bromo-1,1-difluorobut-1-ene before reacting it with the mercapto pyrimidine, mercaptobenzoxazole or mercaptobenzthiazole.

In an alternative procedure, the debromofluorination reaction may be carried out using water as the reaction medium.

As before, zinc, aluminium, or magnesium may be used as the debromofluorinating agent. Mixtures of metals may also be used, for example magnesium with a small proportion of zinc or aluminium. The 4-bromo-1,1-difluorobut-1-ene may conveniently be recovered by distilling it from the reaction mixture, or by extracting it with a water-immiscible solvent according to standard procedures.

In a further alternative procedure for preparing 4-bromo-1,1-difluorobut-1-ene, 1,4-dibromo-1,1,2-trifluorobutane may be debromofluorinated electrolytically, using for example an electrolytic cell containing a solution of a zinc salt (e.g. zinc chloride) and having a lead cathode and a carbon anode.

In this procedure, at the end of a period of electrolysis the contents of the cathode compartment may be transferred to a distillation apparatus, the 4-bromo-1,1-difluorobut-1-ene distilled out and recovered, and the catholyte transferred back to the cathode compartment for re-use. Compounds of Formulas (VI) and (IX) have not been previously reported. In two further aspects, therefore, the invention provides: a compound of Formula (VI) wherein $R^a$ is a $C_{1-4}$ alkyl group or a phenyl group optionally substituted with a $C_{1-4}$ alkyl group; and a compound of Formula (IX) wherein $R^a$ is a $C_{1-4}$ alkyl group or a phenyl group optionally substituted with a $C_{1-4}$ alkyl group. Preferred compounds of Formula (VI) and (IX) for use in the process of the invention are those in which $R^a$ is methyl or para-tolyl, namely 4,4-difluorobut-3-enyl methanesulphonate, 4,4-difluorobut-3-enyl 4-methylbenzenesulphonate, 4-bromo-3,4,4-trifluorobut-3-enyl methanesulphonate, and 4-bromo-3,4,4-trifluorobut-3-enyl 4-methylbenzenesulphonate.

4-Bromo-1,1-difluorobut-1-ene has not previously been reported. In another aspect, therefore, the invention provides this compound, and the process of making it which comprises treating 1,4-dibromo-1,1,2-trifluorobutane with a debromofluorinating agent.

The invention is illustrated by the following Examples in which percentages are by weight and the following abbreviations are used: gc=gas chromatography; nmr=nuclear magnetic resonance; s=singlet; d=doublet; t=triplet; q=quartet; m=multiplet; dd=double doublet; ddt=double doublet of triplets, dtd=double triplet of doublets; b or br=broad; g=grammes; mg=milligrammes; $CDCl_3$=deuterochloroform; Chemical shifts (δ) are measured in parts per million from tetramethylene silane. $CDCl_3$ was used as solvent unless otherwise stated. $M^+$=molecular ion as determined by mass spectrometry; ir=infra red spectrometry; tlc=thin layer chromatography; (dec)=decomposed on melting.

EXAMPLE 1

This example illustrates the preparation of 1,4-dibromo-1,1,2-trifluorobutane.

A solution of 4-bromo-1,1,2-trifluorobut-1-ene (2.5 g) in dry dichloromethane (25 cm$^3$) at 0° C. was heated with HBr gas for 45 minutes. The reaction mixture was then stirred at 0° C. for 1 hour. The reaction mixture was made alkaline with 5% NaHCO$_3$ solution and extracted twice with dichloromethane. The combined dichloromethane extracts were dried (MgSO$_4$), filtered and concentrated under reduced pressure to give a pale yellow liquid (2.84 g). The material was shown by gc analysis to be greater than 99% pure. $^1$H NMR (CDCl$_3$): δ 4.75–5.07(1H,m); 3.42–3.69(2H,m); 2.59–2.15(2H,m).

EXAMPLE 2

This Example illustrates the two step process for the preparation of 4,4-difluorobut-3-enyl 4-methylbenzenesulphonate.

Step 1

4-Bromo-3,4,4-trifluorobutyl 4-methylbenzenesulphonate

To a stirred suspension of silver tosylate (1.03 g) in acetonitrile (10 cm$^3$) at the ambient temperature, protected from the light, was added dropwise 1,4-dibromo-1,1,2-trifluorobutane. The reaction was then heated under reflux for 24 hours after which gc analysis indicated complete consumption of starting material. The reaction mixture was cooled to the ambient temperature and the precipitate was filtered off and washed with ethyl acetate. The filtrate and ethyl acetate washings were combined and washed with water and the aqueous layer extracted with ethyl acetate. The combined ethyl acetate layers were washed with water and brine, dried (MgSO$_4$) and evaporated under reduced pressure to give a brown oil (1.21 g). GC analysis showed this material to be >99% pure. $^1$H NMR (CDCl$_3$): δ 7.80(2H,d); 7.38(2H,d); 4.74(1H,m); 4.19(2H,m); 2.46(3H,s); 2.20(2H, m).

Step 2

4,4-Difluorobut-3-enyl 4-methylbenzenesulphonate

To a stirred suspension of powdered zinc (1.41 g) and iodine (one grain) in methanol (3 cm$^3$) was added a solution of 4-bromo-3,4-difluorobutyl 4-methylbenzenesulphonate (710 mg) in methanol (2 cm$^3$). The reaction mixture was refluxed for 2½ hours after which gc analysis indicated complete consumption of starting material. The organic phase was pipetted from the zinc suspension and the zinc was washed with 3 portions of ethyl acetate. The combined ethyl acetate portions were washed with 2 M hydrochloric acid, dried (MgSO$_4$) and evaporated under reduced pressure to give a brown liquid (470 mg). GC analysis showed this material to be >99% pure. $^1$H NMR (CDCl$_3$): δ 7.79(2H,d); 7.38(2H,d); 4.15(1H,m); 4.01(2H,m); 2.46(3H,s); 2.35(2H, m).

EXAMPLE 3

The general procedure according to the invention for the preparation of 2-(4,4-difluorobut-3-enylthio)-substituted benzoxazoles and benzthiazoles by reaction of the corresponding 2-mercapto heterocycle with 4,4-difluorobut-3-enyl 4-methylbenzenesulphonate is illustrated by the following preparation of 2-(4,4-Difluorobut-3-enylthio) benzoxazole (Compound No. 2).

2-Mercaptobenzoxazole (4.79 g) was added to a solution of 1,1-difluorobut-1-en-4-yl 4-methylbenzenesulphonate (6.4 g) in acetone (200 cm$^3$) containing potassium carbonate (5.06 g). The mixture was heated to reflux overnight (17 hr) and gc used to confirm that the 1,1-difluorobut-1-en-4-yl 4-methylbenzenesulphonate had been consumed and the product had formed. The reaction mass was allowed to cool and was filtered through a plug of High-Flo filter aid to remove insoluble inorganic material. The solid material was washed with ethyl acetate and the combined organic portions evaporated under reduced pressure to give 7.1 g of a brown oily residue. This material was fractionated by eluting through a bed of silica using hexane/ethyl acetate (40:1 by volume) as solvent to give the required product as a colourless oil (5.4 g, 92% based on the sulphonate); M$^+$=241; $^1$H NMR (CDCl$_3$): δ 2.5–2.6 (m 2H), 3.3–3.4 (t 2H), 4.2–4.4 (m 1H), 7.2–7.35 (m 2H), 7.45 (dd 1H), 7.6 (dd 1H).

EXAMPLE 4

The following compounds were prepared from the corresponding 2-mercapto benzoxazole or 2-mercaptobenzthiazole using the method of Example 3. Where the 2-mercapto benzoxazoles and benzthiazoles are not readily available commercially, they may be prepared by the standard procedures desired in the text, for example those illustrated below in Examples 5 and 6.

(a) 2-(4,4-difluorobut-3-enylthio)-5-methylbenzoxazole (Compound No. 41). $^1$H NMR (CDCl$_3$): δ 7.38(1H,s); 7.30(1H,d); 7.03(1H,d); 4.30(1H,m); 3.32(2H,t); 2.69(2H, q); 2.45(3H,s); (oil).

(b) Methyl 2-(4,4-difluorobut-3-enylthio)benzoxazole-6-carboxylate (Compound No. 10). M$^+$=299; $^1$H NMR (CDCl$_3$): δ 2.5–2.6 (m 2H), 3.35 (t 2H), 3.95 (s 3H), 4.2–4.4 (m 1H), 7.65 (d 1H), 8.05 (dd 1H), 8.15 (d 1H); (oil).

(c) 2-(4,4-Difluorobut-3-enylthio)-6-nitrobenzoxazole (Compound No. 5). M$^+$=286; $^1$H NMR (CDCl$_3$): δ 2.55–2.65 (m 2H), 3.35–3.45 (t 2H), 4.25–4.40 (m 1H), 7.65 (d 1H), 8.25 (dd 1H), 8.35 (d 1H); (oil).

(d) 2-(4,4-Difluorobut-3-enylthio)-5-phenylbenzoxazole (Compound No. 26). mp 41–42, 4° C.; M$^+$=317; $^1$H NMR (CDCl$_3$): δ 2.5–2.65 (m 2H), 3.3–3.4 (t 2H), 4.25–4.45 (m 1H), 7.3–7.5 (m 5H), 7.6 (d 2H), 7.8 (s 1H).

(e) 2-(4,4-Difluorobut-3-enylthio)-6-fluorobenzthiazole (Compound No 15). ir 1750 cm$^{-1}$; M$^+$275; $^1$H NMR (CDCl$_3$): δ 2.50(m 2H); 3.35(t 2H); 4.25(m 1H); 7.10(m 1H); 7.40(dd 1H); 7.75(dd 1H); (oil).

(f) 2-(4,4-Difluorobut-3-enylthio)-4-methylbenzthiazole (Compound No 16); M$^+$=271; $^1$H NMR (CDCl$_3$): δ 2.55(m 2H); 2.68(s 3H); 3.40(t 2H); 4.32(m 1H); 7.2(m 2H); 7.60(dd 1H); (oil).

(g) 2(4,4-Difluorobut-3-enylthio)-6-methylbenzthiazole (Compound No 7). M$^+$=271; $^1$H NMR (CDCl$_3$): δ 2.48(s 3H); 2.55(m 2H); 3.35(t 2H); 4.3(double triplet of doublets 1H); 7.20(dd 1H); 7.55(s 1H); 7.75(d 1H); (oil).

(h) 2-(4,4-difluorobut-3-enylthio)-5-methylbenzthiazole (Compound No. 22). $^1$H NMR (CDCl$_3$): δ 7.68(1H,bs); 7.62(1H,d); 7.14(1H, bd); 4.32(1H,dtd): 3.38(2H,t); 2.54 (2H, bq); 2.48(3H,s); (oil).

EXAMPLE 5

A general one-step procedure for the preparation of pyrimidines substituted with a 4,4-difluoro-3-butenylthio group in the 2, 4 or 5-position, starting with a correspondingly substituted mercaptopyrimidine, is illustrated by the following preparation of 2-[(4,4-difluoro-3-butenyl)thiol]-4-phenyl-pyrimidine (Compound No. 2.4) from 4-phenyl-2 (1H)-pyrimidinethione and 4,4-difluoro-3-butenyl 4-methyl-benzenesulfonate.

4-Phenyl-2(1H)-pyrimidinethione (0.29 g), 4,4-difluoro-3-butenyl 4-methyl-benzene sulfonate (0.4 g), potassium carbonate (0.22 g) and potassium iodide (catalytic amount) were mixed in acetone (20 cm$^3$) and heated under reflux for five hours then allowed to cool overnight. The precipitate formed was removed by filtration and the filtrate evaporated under reduced pressure to give an orange solid. Chromatography on silica gel using a 90:10 mixture of hexane:ethyl acetate as eluant gave Compound No. 2.4 as a yellow oil (0.253 g). M$^+$=278; $^1$H NMR (CDCl$_3$): δ 2.48–2.58(2H,m); 3.28(2H,t); 4.24–4.42(1H,m); 7.38(1H,d); 7.48–7.56(3H, m); 8.04–8.12(2H,m); 8.56(1H,d).

The following compounds according to the invention were prepared using the above procedure.

(a) 2-[(4,4-difluoro-3-butenyl)thio]-4-(4-fluorophenyl)-pyrimidine (Compound No. 2.43). M$^+$=296; $^1$H NMR (CDCl$_3$): δ 2.46–2.58(2H,m); 3.26(2H,t); 4.24–4.42(1H,m); 7.14–7.24(2H,m); 7.34(1H,d); 8.04–8.14(2H,m); 8.54(1H, d); (off-white solid mp 44–45° C.).

(b) 4-cyclopropyl-2-[(4,4-difluoro-3-butenyl)thio]-pyrimidine (Compound No. 2.46). M$^+$=242; $^1$H NMR (CDCl$_3$): δ 1.02–1.20(4H,m); 1.84–1.98(1H,m); 2.34–2.48 (2H,m); 3.10(2H,t); 4.18–4.38(1H,m); 6.82(1H,d); 8.26(1H, d); (oil)

(c) 2-[(4,4-difluoro-3-butenyl)thio]-4-(1-methylcyclopropyl)-pyrimidine (Compound No. 2.47). M$^+$=256; $^1$H NMR (CDCl$_3$): δ 0.88–0.94(2H,m); 1.32–1.38 (2H,m); 1.48(3H,s); 2.36–2.48(2H,m); 3.10(2H,t); 4.20–4.38(1H,m); 6.94(1H,d); 8.34(1H,d); (oil).

EXAMPLE 6

This Example illustrates the preparation of 4-bromo-1,1-difluorobut-1-ene.

(a) Preparation of 1,4-dibromo-1,1,2-trifluorobutane.

Commercially available 4-bromo-1,1,2-trifluorobut-1-ene (240 g, 1.27 mol) was washed with water (300 ml) and then with brine (300 ml) and dried (MgSO$_4$) before use. Benzoyl peroxide (ca. 0.7 g) was added in one portion, and hydrogen bromide gas was bubbled through the mixture at such a rate that the reaction temperature was maintained at between 30 to 40° C. After 2 hours, gas chromatography of a sample of the reaction mixture showed that little starting material remained. The reaction mixture was washed with water (300 ml), then with saturated sodium bicarbonate solution, and then again with water (300 ml) dried (MgSO$_4$) and filtered to give a pale yellow oil (296.7 g, 87%) identified as 1,4-dibromo-1,1,2-trifluorobutane. Proton NMR (CDCl$_3$ solution): δ 2.38(2H,m,BrCH$_2$CH$_2$), 3.57(2H,m,Br CH$_2$CH$_2$), and 4.90 (H, m,CHFCF$_2$Br). Gas chromatographic analysis showed that the product was more than 98% pure.

(b) Preparation of 4-bromo-1,1-difluorobut-1-ene.

Zinc powder (0.88 g) was added to a solution of 1-4-dibromo-1,1,2-trifluorobutane (1.38 g) in acetone (6 ml) containing water (one drop), under an atmosphere of nitrogen. The mixture was subjected to ultrasonic radiation while being kept in a bath heated to 55° C. After 45 minutes, gas chromatographic analysis showed that a large proportion of the dibromobutane had been consumed. The mixture was then added to more zinc powder (3 g) in acetone containing a trace of water, which had been pre-heated to 55° C. After a further 20 minutes at this temperature, gas chromatographic analysis of a sample of the reaction mixture indicated that all of the dibromobutane starting material had been consumed, showing that the de-bromofluorination reaction had initiated. More 1,4-dibromo-1,1,2-trifluorobutane (12.34 g) was then added to the reaction mixture over a period of 75 minutes while the reaction mixture was kept at 55° C. Heating was then continued for a further 95 minutes. Gas chromatographic analysis of a sample indicated that about 3% of the dibromobutane remained unchanged. Further zinc powder (0.16 g) was added and heating continued until gc analysis showed that the dibromobutane had been completely consumed. The acetone solution was then decanted from the zinc residues to give a solution of 4-bromo-1,1-difluorobut-1-ene suitable for use in further chemical reactions.

EXAMPLE 7

This Example illustrates the preparation of 2-(4,4-difluorobut-3-enyl)thiobenzthiazole and 2-(4,4-difluorobut-3-enyl)thiobenzoxazole according to the invention.

To the solution of 4-bromo-1,1-difluorobut-1-ene prepared in Example 6 was added potassium carbonate (10.76 g) and 2-mercaptobenzthiazole (9.18 g). The mixture was stirred at 55° C. for 6 hours and then at room temperature overnight. Gas-liquid chromatography of a sample of the reaction mixture showed that a small amount of 4-bromo-1,1-difluorobut-1-ene remained. More potassium carbonate (1.0 g) was added and the mixture heated for another two and a half hours at 55° C., when all of the bromo compound had been consumed. The mixture was cooled to room temperature and filtered. The residue was washed with acetone and the filtrate and washings combined and evaporated under reduced pressure to give the crude product (16.18 g). This was dissolved in dichloromethane. The solution was filtered and washed with dilute sodium hydroxide (2×25 ml) and with brine (2×25 ml), dried over magnesium sulphate, filtered, the filtrate evaporated to give 2-(4, 4-difluorobut-3-enyl)thiobenzthiazole, having a gas chromatographic retention time identical with that of an authentic sample. The yield was 63% based on the quantity of 1,4-dibromo-1,1,2-trifluorobutane used in step (b) of Example 1. 2-(4,4-Difluorobut-3-enyl)thiobenzoxazole was prepared in the same way, but using 2-mercapto benzoxazole instead of 2-mercapto benzthiazole.

EXAMPLE 8

This Example further illustrates the preparation of 4-bromo-1,1-difluorobut-1-ene, by debromofluorination of 1,4-dibromo-1,1,2-trifluorobutane. In this example, catalytic amounts of iodine and zinc iodide were used to initiate the debromofluorination reaction, rather than irradiation with ultra-sound as in Example 6.

1,4-Dibromo-1,1,2-trifluorobutane (8.05 g, 30 mmol) in methanol (3 ml, dried by molecular sieve and purged with nitrogen) was added dropwise over a period of 90 minutes to a mixture of zinc dust (3 g, 1.5 eq., 45 mmol), iodine (catalytic amount), zinc iodide (catalytic amount), and methanol (10 ml dried by molecular sieve) under a nitrogen atmosphere at room temperature. The reaction mixture was stirred for a further 10 minutes after addition was complete, and then filtered through a small bed of silica. Water (20 ml) was added to the filtrate and the organic layer separated (2.65 g, 53%). The organic layer was distilled in a Kugelrohr apparatus (Buchi GKR-51) at an oven temperature of 90° C. to give a clear oil identified as 4-bromo-1,1-difluorobut-1-ene. Proton NMR: δ 2.56(2H,q,CH$_2$CH2Br), 3.4(2H,t,CH$_2$ CH$_2$Br), and 4.3(1H,dt,CF$_2$=CH)

EXAMPLE 9

This Example illustrates the preparation of 4-[(4,4-difluoro-3-butenyl)thio]-pyrimidine. 4-Bromo-1,1-difluorobut-1-ene (1.86 g), 4(3H)pyrimidinethione (1.12 g), potassium carbonate (5 g) and acetone (60 ml) is heated and stirred under reflux for 5 hours, cooled, and filtered. The filtrate is evaporated and the residue chromatographed on silica gel using a mixture of ethyl acetate and hexane as eluent to give 4-[(4,4-difluoro-3-butenyl)thio]-pyrimidine as an oil.

EXAMPLE 10

This Example illustrates the preparation of 4-bromo-1,1-difluorobut-1-ene in water as the reaction medium.

Zinc powder (98 g) was stirred in water (400 ml) and iodine (0.6 g) was added as a catalyst. Stirring was continued and the slurry was heated to 80–85° C. under an atmosphere of nitrogen. 1,4-Dibromo-1,1,2-trifluorobutane (281.5 g) was added dropwise over a period of 2.5 hours. After addition was complete, heating was continued for a further 2.5 hours, when gas-liquid chromatography confirmed that all of the starting material had been consumed. The product, 4-bromo-1,1-difluorobut-1-ene, was distilled from the reaction mixture. The bulk of the product was collected at a head temperature of 77.3° C. The product was collected up to a head temperature of 100° C.

The yield of product was 132.2 g, having a purity of 94% as measured by gc.

EXAMPLE 11

This Example illustrates the preparation of 4-bromo-1,1-difluorobut-1-ene by electrochemical dehalogenation of 1,4-dibromo-1,1,2-trifluorobutane.

A solution of zinc chloride (2.0 g) in de-ionised water (40 ml) was charged to the cathode compartment of a small laboratory scale electrolyte cell. Some of the solution was allowed to diffuse through glass frit cell divider (30 mm diameter) and into the anode compartment. The cathode consisted of a lead disc (diameter 25 mm) mounted parallel to and 25 mm away from the cell divider. The anode consisted of a single graphite rod, 12 mm in diameter. 1,4-Dibromo-1,1,2-trifluorobutane (5.0 g) was charged to the cathode compartment, which was stirred with a magnetic stirring bar. A little surface-active agent was added to assist in dispersing the 1,4-dibromo-1,1,2-trifluorobutane. A current of 1.0 amp was passed through the cell for 2 hours, when gc analysis showed that only 2% of untreated starting material remained. The contents of the cathode compartment were distilled and the distillate collected up to a head temperature of 100° C. The yield of 4-bromo-1,1-difluoro-but-1-ene, identified by its NMR spectrum, was 1.4 g.

EXAMPLE 12

This Example illustrates the preparation of 4-bromo-1,1-difluorobut-1-ene by dehalogenation of 1,4-dibromo-1,1,2-trifluorobutane with aluminium metal using water as the reaction medium.

Aluminium powder (0.4 g) was suspended in water (10 ml), and a crystal of iodine and concentrated hydrochloric acid (3 drops) were added. 1,4-Dibromo-1,1,2-trifluorobutane (270 g) was added, and the mixture stirred at room temperature until the colour of the iodine was discharged. The reaction mixture was then heated to 67° C. overnight (18 hours) with stirring, when gc analysis showed that only 2% of untreated starting material remained. The product was distilled from the reaction mixture and the distillate passing over at between 65° C. and 100° C. was collected. The yield of 4-bromo-1,1-difluorobut-1-ene was 0.74 g.

This was analysed by gc and found to be 83.7% pure. The identity of the product was confirmed by NMR.

CHEMICAL FORMULEA
(IN DESCRIPTION)

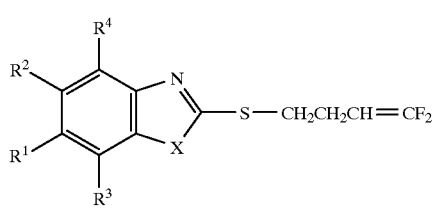

(IV)

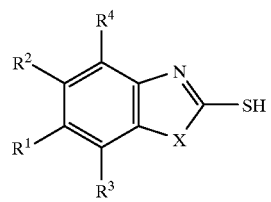

(V)

$CF_2=CHCH_2CH_2OSO_2R^a$ (VI)

$CF_2=CFCH_2CH_2Br$ (VII)

$CF_2BrCHFCH_2CH_2Br$ (VIII)

$CF_2BrCHFCH_2CH_2OSO_2R^a$ (IX)

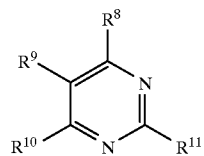

(X)

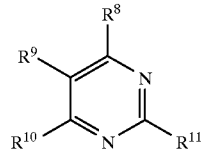

(XI)

(One of $R^8$ — $R^{11}$ is SH)

We claim:

1. A compound of formula IX:

$CF_2BrCHFCH_2CH_2OSO_2R^a$     IX:

wherein $R^a$ is $C_{1-4}$ alkyl or phenyl optionally substituted by $C_{1-4}$ alkyl.

2. A process for preparing 4-bromo-1,1-difluoro-but-1-ene which comprises treating 1,4-dibromo-1,1,2-trifluorobutane with a debromofluorinating agent.

3. A process as claimed in claim 2 wherein the debromofluorination reaction is carried out in a reaction medium consisting essentially of water.

* * * * *